(12) United States Patent
Takegawa et al.

(10) Patent No.: US 8,663,948 B2
(45) Date of Patent: Mar. 4, 2014

(54) HOST, TRANSFORMANT AND METHOD FOR PRODUCING THE TRANSFORMANT AND METHOD FOR PRODUCING O-GLYCOSYLATED HETEROLOGOUS PROTEIN

(75) Inventors: Kaoru Takegawa, Fukuoka (JP); Yuko Hama, Tokyo (JP); Chihiro Hama, legal representative, Tokyo (JP); Hideki Tohda, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 28 days.

(21) Appl. No.: 13/077,333

(22) Filed: Mar. 31, 2011

(65) Prior Publication Data

US 2011/0287481 A1 Nov. 24, 2011

Related U.S. Application Data

(63) Continuation of application No. PCT/JP2009/067081, filed on Sep. 30, 2009.

(30) Foreign Application Priority Data

| Oct. 1, 2008 | (JP) | ................. | 2008-256354 |
| May 15, 2009 | (JP) | ................. | 2009-119280 |

(51) Int. Cl.

| C12P 21/06 | (2006.01) |
| C12P 1/00 | (2006.01) |
| C12P 19/00 | (2006.01) |
| C12P 19/44 | (2006.01) |
| C12P 19/18 | (2006.01) |
| C12P 19/04 | (2006.01) |
| C12N 15/09 | (2006.01) |
| C12N 15/00 | (2006.01) |
| C12N 15/74 | (2006.01) |
| C12N 1/00 | (2006.01) |

(52) U.S. Cl.
USPC ............ 435/41; 435/69.1; 435/69.4; 435/72; 435/74; 435/97; 435/101; 435/440; 435/471; 435/476; 435/477; 435/243; 435/254.1; 435/254.11

(58) Field of Classification Search
None
See application file for complete search history.

(56) References Cited

U.S. PATENT DOCUMENTS

| 2002/0068325 A1 | 6/2002 | Ng et al. |
| 2011/0143396 A1* | 6/2011 | Choi .......................... 435/69.6 |

FOREIGN PATENT DOCUMENTS

| EP | 0 773 296 | 5/1997 |
| EP | 1 505 149 | 2/2005 |
| JP | 2004-501642 | 1/2004 |
| JP | 2005-514021 | 5/2005 |

OTHER PUBLICATIONS

Lussier et al., Functional Characterization of the YUR1, KTR1, and KTR2 Genes as Members of the Yeast KRE2/MNT1 Mannosyltransferase Gene Family; J Biol Chem, vol. 271, No. 18, pp. 11001-11008, 1996.*
Aslett et al., Gene Ontology annotation status of the fission yeast genome: preliminary coverage approaches 100%; Yeast, vol. 23, No. 913-919, 2006.*
Aslett et al., Gene Ontology annotation status of the fission yeast genome: preliminary coverage approaches 100%; Yeast, vol. 23, No. 913-919, 2006 supplemental data, p. 15 of 369.*
International Search Report issued Dec. 28, 2009 in PCT/JP09/067081 filed Dec. 21, 2009.
http://www.ncbi.nlm.nih.gov/nuccore/68012314 Schizosaccharomyces pombe alpha-1,2-mannosyltransferase (SPBC19C7.12c) partial mRNA (2009) 4 pages.
Gemmill, TR et al., "Schizosaccharomyces pombe produces novel $Gal_{0-2}Man_{1-3}$ O-linked oligosaccharides", Glycobiology, vol. 9, No. 5, (1999) p. 507-515.
Lussier, M. et al., "The KTR and MNNI mannosyltransferase familes of Saccharomyces cerevisiae", Biochimica Biophysica Acta, (1999) vol. 1426, No. 2, p. 323-334.
Lussier, M. et al., "Functional characterization of the YUR1, KTR1, and KTR2 Genes as Members of the Yeast KRE2/MNT1 Mannosyltransferase Gene Family", J. Biol. Chem., (1996), vol. 271, No. 18, p. 11001-11008.
Ikeda, Y. et al., "Identification and characterization of a gene required for α1,2-mannose extension in the O-linked glycan synthesis pathway in Schizosaccharomyces pombe", FEMS Yeast Res, (2009), vol. 9, No. 1, p. 115-125.

(Continued)

Primary Examiner — Celine Qian
Assistant Examiner — Addison D Ault
(74) Attorney, Agent, or Firm — Oblon, Spivak, McClelland, Maier & Neustadt, L.L.P.

(57) ABSTRACT

The object is to provide a transformant which can produce a heterologous protein having a structurally controlled O-linked sugar chain having an O-Man-Gal disaccharide structure, a method for producing the transformant by using Schizosaccharomyces pombe as the host, and provide a host for producing the transformant and a method for producing an O-glycosylated heterologous protein.
An Schizosaccharomyces pombe host having no omh1 gene or an inactivated omh1 gene in its chromosomes for producing an O-glycosylated heterologous protein having an O-linked sugar chain having an O-Man-Gal disaccharide structure by expression of the heterologous protein by a genetic engineering technique and subsequent glycosylation of the expressed heterologous protein. A transformant from the host, a method for producing the transformant and a method for producing an O-glycosylated heterologous protein by using the transformant.

11 Claims, 7 Drawing Sheets

(56) References Cited

OTHER PUBLICATIONS

Strahl-Bolsinger S. et al., "Protein 0-mannosylation", Biochimica et Biophysica Acta (1999) p. 297-307.

Girrbach V., et al., "Members of the Evolutionarily Conserved PMT Family of Protein O-Mannosyltransferases Form Distinct Protein Complexes among Themselves", Journal Biological Chemistry, vol. 278, No. 14, (2003) p. 12554-12562.

Extended European Search Report w/Search Opinion as received in the corresponding European Patent Application No. 09817834.6-1212/2341139 dated Nov. 13, 2012.

Clinton E. Ballou, et al., "*Schizosaccharomyces pombe* glycosylation mutant with altered cell surface properties", Proc. Natl. Acad. Sci. USA, vol. 91, pp. 9327-9331, Sep. 1994.

M. Lucas, et al., "Sequence analysis of two cosmids from the right arm of the *Schizosaccharomyces pombe* chromosome II", Yeast 2000: 16: 299-306.

Database UniProt [Online], Aug. 1, 1998, RecName: Full=Uncharacterized mannosyltransferase C19C7. 12c; EC=2.4.1; XP002686400.

Office Action as received in the corresponding Chinese Patent Application No. 200980139731.1 dated Sep. 29, 2013 w/English Translation.

Wood, et al., "*Schizosaccharomyces pombe* 972h-alpha-1,2-mannosyltransf", Nature 415 (6874), pp. 871-880, (2002), Accession NM_001022088.

* cited by examiner

Fig. 1.

(a) Wild type (b) omh1 mutant (c) omh2 mutant (d) omh3 mutant (e) omh4 mutant (f) omh5 mutant (g) omh6 mutant

SEQUENCE LISTING

```
<160> NUMBER OF SEQ ID NOS: 28

<210> SEQ ID NO 1
<211> LENGTH: 12
<212> TYPE: PRT
<213> ORGANISM: Schizosaccharomyces cerevisiae

<400> SEQUENCE: 1

Tyr Asn Leu Cys His Phe Trp Ser Asn Phe Glu Ile
1               5                   10

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 2
ggaagccata ttcgaagtac tatagtg                                          27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcaatggatt cataaggatc acagtcgc                                         28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaagtggata gcgtctactt ttaatggtg                                        29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tccctttcta gggcaatgaa gaagaggagc                                       30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctggcgtatc ttacacaatc gaaccatg                                         28

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgtcgcat gcgactgtac atccgtaggg c                                     31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 8
gtttctcgag atcccagtga ttcagccacc                                           30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtttaagctt gcactatcag tagtaagacc                                           30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtttgaattc gccagagtta aaagctaggg                                           30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtttggatcc tgtttggcca caccgtcacc                                           30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtttggatcc ataatgtgtt gactcgcagg                                           30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtttgaattc tcttctattc tctaacgacc                                           30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```

```
gtttaagctt aatacgggta ctttacgctc                                              30
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 15

```
gtttctcgag catcacatca ttaacaggcc                                              30
```

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 16

```
gtttggatcc tgtgcattat gaacaaccac                                              30
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

```
gtttgaattc agaagcactc aaattggagc                                              30
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 18

```
gtttaagctt ttgatgaatg agctttacag                                              30
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 19

```
gtttggtacc cttttttgac tgcttgttcc                                              30
```

<210> SEQ ID NO 20
<211> LENGTH: 325
<212> TYPE: PRT
<213> ORGANISM: Schizosaccharomyces cerevisiae

<400> SEQUENCE: 20

```
Ala Gly Lys Pro Lys Ala Cys Tyr Val Thr Leu Val Arg Asn Lys Glu
1               5                   10                  15

Leu Lys Gly Leu Leu Ser Ser Ile Lys Tyr Val Glu Asn Lys Ile Asn
            20                  25                  30
```

Lys Lys Phe Pro Tyr Pro Trp Val Phe Leu Asn Asp Glu Pro Phe Thr
            35                  40                  45

Glu Glu Phe Lys Glu Ala Val Thr Lys Ala Val Ser Ser Glu Val Lys
 50                  55                  60

Phe Gly Ile Leu Pro Lys Glu His Trp Ser Tyr Pro Glu Trp Ile Asn
65                  70                  75                  80

Gln Thr Lys Ala Ala Glu Ile Arg Ala Asp Ala Thr Lys Tyr Ile
                85                  90                  95

Tyr Gly Gly Ser Glu Ser Tyr Arg His Met Cys Arg Tyr Gln Ser Gly
                100                 105                 110

Phe Phe Trp Arg His Glu Leu Glu Glu Tyr Asp Trp Tyr Trp Arg
                115                 120                 125

Val Glu Pro Asp Ile Lys Leu Tyr Cys Asp Ile Asn Tyr Asp Val Phe
                130                 135                 140

Lys Trp Met Gln Glu Asn Glu Lys Val Tyr Gly Phe Thr Val Ser Ile
145                 150                 155                 160

His Glu Tyr Glu Val Thr Ile Pro Thr Leu Trp Gln Thr Ser Met Asp
                165                 170                 175

Phe Ile Lys Lys Asn Pro Glu Tyr Leu Asp Glu Asn Asn Leu Met Ser
                180                 185                 190

Phe Leu Ser Asn Asp Asn Gly Lys Thr Tyr Asn Leu Cys His Phe Trp
                195                 200                 205

Ser Asn Phe Glu Ile Ala Asn Leu Asn Leu Trp Arg Ser Pro Ala Tyr
                210                 215                 220

Arg Glu Tyr Phe Asp Thr Leu Asp His Gln Gly Gly Phe Phe Tyr Glu
225                 230                 235                 240

Arg Trp Gly Asp Ala Pro Val His Ser Ile Ala Ala Leu Phe Leu
                245                 250                 255

Pro Lys Asp Lys Ile His Tyr Phe Ser Asp Ile Gly Tyr His His Pro
                260                 265                 270

Pro Tyr Asp Asn Cys Pro Leu Asp Lys Glu Val Tyr Asn Ser Asn Asn
                275                 280                 285

Cys Glu Cys Asp Gln Gly Asn Asp Phe Thr Phe Gln Gly Tyr Ser Cys
290                 295                 300

Gly Lys Glu Tyr Tyr Asp Ala Gln Gly Leu Val Lys Pro Lys Asn Trp
305                 310                 315                 320

Lys Lys Phe Arg Glu
                325

<210> SEQ ID NO 21
<211> LENGTH: 316
<212> TYPE: PRT
<213> ORGANISM: Schizosaccharomyces cerevisiae

<400> SEQUENCE: 21

Leu Val Arg Asn Arg Asp Leu Tyr Ser Leu Ala Glu Ser Ile Lys Ser
1               5                   10                  15

Val Glu Asp Arg Phe Asn Ser Lys Phe Asn Tyr Asp Trp Val Phe Leu
                20                  25                  30

Asn Asp Glu Glu Phe Thr Asp Glu Phe Lys Asn Val Thr Ser Ala Leu
                35                  40                  45

Val Ser Gly Thr Thr Lys Tyr Gly Val Ile Pro Lys Glu His Trp Ser
            50                  55                  60

Phe Pro Glu Trp Ile Asp Glu Glu Lys Ala Ala Gln Val Arg Lys Glu
65                  70                  75                  80

```
Met Gly Glu Lys Arg Ile Ile Tyr Gly Asp Ser Ile Ser Tyr Arg His
            85                  90                  95

Met Cys Arg Phe Glu Ser Gly Phe Phe Tyr Arg His Pro Leu Met Asp
            100                 105                 110

Asp Tyr Asp Trp Tyr Trp Arg Val Glu Pro Asp Ile Lys Leu His Cys
            115                 120                 125

Asp Ile Asp Tyr Asp Val Phe Lys Phe Met Lys Asp Asn Lys Lys Lys
        130                 135                 140

Tyr Ala Phe Ala Ile Ser Ile Lys Glu Tyr Glu Ala Thr Ile Pro Thr
145                 150                 155                 160

Leu Trp Glu Thr Thr Arg Lys Phe Met Glu Ala His Pro Glu Leu Ile
                165                 170                 175

His Glu Asn Asn Met Leu Asp Phe Val Ser Asp Gln Gly Leu Ser
            180                 185                 190

Tyr Asn Leu Cys His Phe Trp Ser Asn Phe Glu Ile Ala Ala Leu Asp
            195                 200                 205

Leu Trp Arg Ser Pro Ala Tyr Ser Ala Tyr Phe Asp Tyr Leu Asp Arg
        210                 215                 220

Glu Gly Gly Phe Phe Tyr Glu Arg Trp Gly Asp Ala Pro Val His Ser
225                 230                 235                 240

Ile Gly Ala Ala Leu Phe Leu Asp Arg Ser Glu Ile His His Phe Gly
                245                 250                 255

Asp Ile Gly Tyr Tyr His Val Pro Phe His Ser Cys Pro Ile Asp Thr
            260                 265                 270

Ser Ile Arg Leu Ala Asn Lys Cys Asp Cys Asp Pro Ser Lys Asp Phe
        275                 280                 285

Thr Trp His Ser Tyr Ser Cys Thr Thr Lys Phe Tyr Asn Ile Asn Lys
            290                 295                 300

Leu Pro Lys Pro Ala Gly Trp Gln Asn His Ile Gly
305                 310                 315

<210> SEQ ID NO 22
<211> LENGTH: 312
<212> TYPE: PRT
<213> ORGANISM: Schizosaccharomyces cerevisiae

<400> SEQUENCE: 22

Leu Ala Arg Asn Ser Asp Leu Trp Asn Leu Val Lys Ser Ile Arg His
1               5                   10                  15

Val Glu Asp Arg Phe Asn Asn Arg Tyr His Tyr Asp Trp Val Phe Leu
            20                  25                  30

Asn Asp Gln Pro Phe Ser Asp Glu Phe Lys Arg Val Thr Ser Ala Leu
        35                  40                  45

Val Ser Gly Lys Ala Lys Tyr Gly Thr Ile Pro Lys Asp His Trp Ser
50                  55                  60

Ile Pro Ser Trp Ile Asp Thr Glu Lys Phe Asp Glu Lys Arg Leu Ala
65                  70                  75                  80

Met Gly Lys Leu Asp Ile Pro Tyr Gly Ser Ser Val Pro Tyr Arg His
            85                  90                  95

Met Cys Arg Phe Gln Ser Gly Phe Ile Trp Arg His Pro Leu Leu Glu
            100                 105                 110

Glu Tyr Glu Trp Phe Trp Arg Val Asp Thr Asp Ile Thr Leu Phe Cys
        115                 120                 125

Asp Ile Gln Tyr Asp Ile Phe Lys Phe Leu Lys Val Asn Asn Lys Lys
        130                 135                 140
```

Tyr Gly Phe Ile Leu Ser Val Ser Glu Tyr Glu Arg Thr Ile Pro Thr
145                 150                 155                 160

Leu Trp Glu Thr Thr Lys Lys Phe Ile Lys Lys Asn Pro Lys Phe Leu
            165                 170                 175

His Lys Asn Asn Leu Met Lys Phe Ile Ser Asn Asp Asp Gly Asp Thr
        180                 185                 190

Tyr Asn Met Cys His Phe Trp Thr Asn Phe Glu Ile Gly Ser Leu Asp
    195                 200                 205

Phe Phe Arg Ser Asp Ala Tyr Arg Glu Tyr Asp Tyr Leu Asp Ser
210                 215                 220

Ser Gly Gly Phe Phe Tyr Glu Arg Trp Gly Asp Ala Pro Val His Ser
225                 230                 235                 240

Ile Ala Ala Ser Leu Phe Leu Asp Lys Ser Glu Ile His Phe Asp
                245                 250                 255

Gly Leu Gly Phe His His Pro Asp Phe Thr Ser Cys Pro Ile Glu Gln
                260                 265                 270

Lys Ile Arg Leu Gln Asn Lys Cys Ile Cys Glu Pro Ser Lys Asp Val
            275                 280                 285

Thr Trp Thr Pro Asp Tyr Phe Cys Thr Arg Lys Tyr Phe Ser Ala Gly
290                 295                 300

Asn Tyr Lys Leu Pro Pro Gly Ile
305                 310

<210> SEQ ID NO 23
<211> LENGTH: 314
<212> TYPE: PRT
<213> ORGANISM: Schizosaccharomyces pombe

<400> SEQUENCE: 23

Leu Ala Arg Asn Glu Asp Leu Asn Asp Leu Leu Lys Ser Ile Arg Lys
1               5                   10                  15

Leu Glu Lys Thr Phe Asn His Lys Tyr His Tyr Gly Trp Val Phe Leu
            20                  25                  30

Asn Asn Glu Glu Phe Ser Asp Glu Phe Lys Glu His Val Ile Glu Ala
        35                  40                  45

Val Ser Gly Lys Cys Glu Phe Gly Leu Val Pro Gln Glu Gln Trp Ser
50                  55                  60

Ile Pro Glu Tyr Ile Asp Gln Asp Lys Met His Glu Asn Trp Lys Lys
65                  70                  75                  80

Leu Gln Glu Leu Gly Ile Leu Tyr Ala Asp Lys Glu Ser Tyr Arg His
                85                  90                  95

Met Cys Arg Phe Glu Ser Gly Phe Phe Tyr Arg His Pro Leu Val Gln
            100                 105                 110

Lys Tyr Glu Tyr Tyr Trp Arg Val Glu Pro Ser Val Asp Phe Phe Cys
        115                 120                 125

Asp Leu Asp Phe Asp Pro Phe Ala Tyr Met Lys Glu Asn Asn Lys Ala
130                 135                 140

Tyr Ala Phe Thr Ile Thr Val Thr Glu Tyr Ser Glu Thr Ile Pro Ser
145                 150                 155                 160

Leu Trp Pro Ser Thr Lys Glu Phe Ile Lys Met His Pro Asn Ala Leu
                165                 170                 175

His Pro Asn Asn Ala Leu Asn Phe Ile Ser Asn Asp Asp Gly Glu Thr
            180                 185                 190

Tyr Asn Gly Cys His Phe Trp Thr Asn Phe Glu Ile Ala Lys Val Asp
        195                 200                 205

```
Phe Trp Glu Ser Glu Val Tyr Ser Lys Tyr Phe Asp Tyr Leu Asp Lys
    210                 215                 220
Ser Gly Asn Phe Phe Tyr Glu Arg Trp Gly Asp Ala Pro Val His Ser
225                 230                 235                 240
Ile Ala Val Ser Leu Phe Ala Asp Arg Asp Asn Ile His Phe Phe Asn
                245                 250                 255
Glu Ile Gly Tyr Trp His Pro Gly Ser Gly His Cys Pro Leu Asp Asp
                260                 265                 270
Ala Thr Arg Ala Lys Cys Asp Cys Asp Pro Tyr Glu Ser Ile Asp Tyr
            275                 280                 285
Asn Gly Trp Ser Cys Leu Asp Lys Phe Tyr Thr Ala Phe Glu Met Pro
290                 295                 300
Phe Pro Glu Asn Trp Ser Phe Tyr Ser His
305                 310
```

<210> SEQ ID NO 24
<211> LENGTH: 304
<212> TYPE: PRT
<213> ORGANISM: Schizosaccharomyces pombe

<400> SEQUENCE: 24

```
Leu Ala Arg Asn Ala Asp Leu Tyr Asp Leu Ile Glu Thr Ile Asn Ile
1               5                   10                  15
Tyr Glu Asn Arg Phe Asn Ser Lys His Asn Tyr Pro Trp Val Phe Leu
                20                  25                  30
Asn Asp Glu Pro Phe Thr Arg Thr Phe Glu Val Val Met Ser Arg Leu
            35                  40                  45
Thr Ser Gly Pro Thr Tyr Phe Gly Val Val Asn Ser Ser Glu Trp Asp
    50                  55                  60
Ile Pro Lys Trp Ile Asp Met Asp Ile Ala His Ser Asn Trp Asn Arg
65                  70                  75                  80
Leu Ser Arg Glu Gly Val Leu Tyr Gly Gly Met Lys Ser Tyr Arg Gln
                85                  90                  95
Met Cys Arg Tyr Phe Ser Gly Phe Phe Trp Arg His Pro Leu Leu Asp
                100                 105                 110
Pro Tyr Lys Tyr Tyr Trp Arg Val Glu Pro Ser Thr Lys Leu Leu Cys
            115                 120                 125
Glu Val Asn Lys Asp Pro Phe Arg Gln Leu Arg Leu Leu Asn Lys Thr
    130                 135                 140
Tyr Gly Phe Val Ile Thr Leu Phe Glu Ile Gly Gln Thr Val Pro Ser
145                 150                 155                 160
Leu Trp Asn Ser Thr Leu Glu Phe Ile Glu Lys Tyr Pro Glu Thr Leu
                165                 170                 175
Ala Lys Asn Asn Leu Trp Glu Trp Ile Ser Asp Asp Asn Gly Lys Lys
                180                 185                 190
Phe Ser His Cys His Phe Trp Ser Asn Phe Glu Ile Ala Asp Leu Asp
            195                 200                 205
Phe Phe Arg Ser Asp Ser Tyr Arg Lys Tyr Phe Asp Phe Leu Asp Lys
    210                 215                 220
Lys Gly Gly Phe Phe Tyr Glu Arg Trp Gly Asp Ala Pro Val His Ser
225                 230                 235                 240
Ile Ala Leu Ser Leu Phe Leu Asp Arg Asn Lys Leu His Tyr Phe Asp
                245                 250                 255
Glu Ile Gly Tyr Ser His Ala Pro Leu Leu His Cys Pro Arg Lys Gly
                260                 265                 270
```

```
Arg Cys Phe Cys Lys Pro Glu Glu Ile Asp Leu Ser Ser Asn Ser Ser
            275                 280                 285

Cys Ile Ala Arg Phe Ile Asn Leu Thr Asn Glu Asp Tyr Asp Glu Leu
        290                 295                 300
```

<210> SEQ ID NO 25
<211> LENGTH: 317
<212> TYPE: PRT
<213> ORGANISM: Schizosaccharomyces pombe

<400> SEQUENCE: 25

```
Pro Asn Met Asn Ala Thr Leu Phe Met Leu Cys Arg Asn Arg Asp Ile
1               5                   10                  15

Lys Asp Ala Leu Val Ser Ile Gln Ser Val Glu Asp Arg Phe Asn His
            20                  25                  30

Arg Tyr His Tyr Pro Trp Thr Phe Met Asn Asp Ala Pro Phe Thr Lys
        35                  40                  45

Glu Phe Ile Thr Ala Thr Ser Lys Met Val Ser Gly Asp Ala Thr Tyr
    50                  55                  60

Val Gln Leu Asn Asn Glu Glu Trp Gly Ile Pro Ile Asn Ile Asp Leu
65                  70                  75                  80

Asn Arg Met Leu Lys Ser Ile Arg Asp Met Thr Asp Asp Lys Val Ile
                85                  90                  95

Tyr Gly Phe Ser Leu Ser Tyr Arg Ile Met Cys Arg Phe Asn Ser Gly
            100                 105                 110

Phe Phe Tyr Arg Asn Lys Ala Leu Ser His Tyr Asp Tyr Tyr Trp Arg
        115                 120                 125

Val Glu Pro Gly Val Glu Tyr Ser Cys Asp Ile Pro Tyr Asp Pro Phe
    130                 135                 140

Arg Lys Leu Ser Asp Glu Asn Lys Ala Tyr Gly Phe Val Ile Ser Met
145                 150                 155                 160

Thr Asp Tyr Tyr Glu Thr Leu Pro Ser Leu Trp Asn Val Thr Arg Asp
                165                 170                 175

Phe Ile His Gln Asn Pro Gln Tyr Leu Ala Gln Asn Asn Ser Leu Asp
            180                 185                 190

Phe Ile Val Asn Asp His Gln Gly Leu Ser Gly Asp Tyr Asn Leu Cys
        195                 200                 205

His Phe Trp Ser Asn Phe Glu Ile Ala Asn Leu Asn Phe Phe Arg Ser
    210                 215                 220

Pro Ala Tyr Thr Asp Tyr Phe Ala His Leu Asp Lys Asn Tyr Gly Phe
225                 230                 235                 240

Phe Tyr Glu Arg Trp Gly Asp Ala Pro Val His Ser Leu Ala Ala Ser
                245                 250                 255

Leu Phe Leu Asn Lys Ser Gln Ile His Tyr Phe Glu Asp Phe Gly Tyr
            260                 265                 270

Tyr His Leu Pro Trp Tyr His Cys Pro Thr Asp Val Gln Ser His Ala
        275                 280                 285

Thr Ala Arg Cys Leu Cys Asp Pro Thr Gly Thr Ile Asp Tyr Leu Pro
    290                 295                 300

Phe Ser Cys Ala Ile Lys Trp Leu Glu Asn Ile Asn Ser
305                 310                 315
```

<210> SEQ ID NO 26
<211> LENGTH: 342
<212> TYPE: PRT
<213> ORGANISM: Schizosaccharomyces pombe

```
<400> SEQUENCE: 26

Leu Ala Arg Asn Ser Asp Leu Pro Gly Val Ser Ser Ile Asn Ser
1               5                   10                  15

Leu Glu Lys His Phe Asn Arg His Phe Asn Tyr Pro Tyr Thr Phe Leu
            20                  25                  30

Asn Asp Glu Pro Phe Asp Glu Lys Phe Lys Glu Thr Ile Leu Lys Leu
        35                  40                  45

Thr Ser Ala Asn Val Glu Phe Gly Thr Leu Glu Lys Asp Thr Phe Gly
    50                  55                  60

Phe Pro Gly Asn Val Asp Val Asp Ala Ala Arg Glu Ala Ile Ala Ser
65                  70                  75                  80

Gln Gly Asp Arg Gly Ile Met Tyr Gly Asp Thr Glu Ser Tyr His His
                85                  90                  95

Met Cys Arg Phe Phe Ser Gly Phe Tyr Lys His Pro Leu Leu Leu
            100                 105                 110

Lys Tyr Gln Trp Tyr Trp Arg Val Glu Pro Asp Val Ala Phe Thr Cys
            115                 120                 125

Asp Ile Ser Tyr Asp Pro Phe Tyr Tyr Met Glu Glu Asn Gly Lys Ile
130                 135                 140

Tyr Gly Tyr Val Val Ala Leu Lys Glu Leu Glu Asp Thr Val Pro Asn
145                 150                 155                 160

Leu Phe Arg Tyr Thr Ser Ala Tyr Arg Arg Asn Asn Asn Leu Thr Ser
                165                 170                 175

Asn Met Trp Lys Phe Phe Leu Asp Ala Pro Lys Lys Glu Asn Tyr Asp
            180                 185                 190

Ile Ser Arg Lys Asp Pro Thr Val Gly Leu Ser Phe Ser Ser His Leu
            195                 200                 205

Asn Ala Met Ile Asp Ser Ser Tyr Ser Ala Glu Thr Ser Ser Met Glu
        210                 215                 220

Gly Glu Ser Tyr Asn Met Cys His Phe Trp Ser Asn Phe Glu Ile Ala
225                 230                 235                 240

Asn Phe Lys Phe Phe Arg Asn Glu Gln Tyr Glu Asn Phe Phe Arg Thr
                245                 250                 255

Met Asp Ala Thr Gly Gly Phe Trp Thr Glu Arg Trp Gly Asp Ala Pro
            260                 265                 270

Phe His Ser Leu Ala Ala Gly Leu Phe Leu Ser Lys Glu Gln Val His
        275                 280                 285

Tyr Phe Arg Asp Leu Gly Tyr Arg His Ser Asp Ile His His Cys Gly
    290                 295                 300

Gln Ser Leu Gly Cys Asn Cys Glu Cys Ile Pro Glu Leu Ser Glu Ile
305                 310                 315                 320

Glu Ser Thr Ser Gly Gly Cys Val Thr Gln Trp Val Asn Leu Ile Gly
                325                 330                 335

Asp Gly Phe Leu Asp Glu
            340

<210> SEQ ID NO 27
<211> LENGTH: 331
<212> TYPE: PRT
<213> ORGANISM: Schizosaccharomyces pombe

<400> SEQUENCE: 27

Leu Ala Arg Asn Ser Asp Leu Asp Gly Val Leu Ser Ser Met Asn Ser
1               5                   10                  15
```

-continued

```
Ile Glu Arg Arg Phe Asn Arg His Phe Lys Tyr Pro Tyr Val Phe Leu
            20                  25                  30

Asn Asp Glu Pro Phe Thr Thr Glu Phe Lys Lys Ala Val Lys Asp Ala
        35                  40                  45

Thr Asp Ser Ser Ile Gln Phe Gly Val Leu Asp Glu Leu Trp Asn
    50                  55                  60

Phe Pro Lys Asp Val Asp Lys Asp Met Ile Asp Glu Ser Ile Ala Glu
65                  70                  75                  80

Gln Val Gly Val Val Tyr Ala Asn Phe Pro Ser Tyr His Lys Met Cys
                85                  90                  95

Arg Phe Phe Ser Arg Asn Phe Tyr Lys His Pro Leu Met Gln Gln Tyr
            100                 105                 110

Glu Trp Tyr Trp Arg Leu Glu Pro Glu Val Thr Phe Ser Cys Asp Ile
        115                 120                 125

Ser Tyr Asp Pro Phe Tyr Tyr Met Asp Lys His Asn Lys Val Tyr Gly
    130                 135                 140

Tyr Val Ile Ala Ile Lys Glu Leu Ala Lys Thr Val Pro Asn Leu Phe
145                 150                 155                 160

Arg Tyr Thr Val Ala His Gln Lys Ile Ser Asn Leu Pro Thr Thr Asp
                165                 170                 175

Leu Trp Ser Phe Phe Leu Asp Lys Arg Tyr Glu Thr Arg Ile Lys Lys
            180                 185                 190

Leu Lys Glu Glu Gln Lys Asp Gln Gly Tyr Tyr Val Leu Pro Glu Pro
        195                 200                 205

Pro Leu Asn Arg Ile Asp Gly Gln Ile Tyr Asn Leu Cys His Phe Trp
    210                 215                 220

Ser Asn Phe Glu Ile Ala Arg Leu Asp Phe Tyr Asn Ser Lys Glu Tyr
225                 230                 235                 240

Asn Glu Tyr Val Asp Ala Leu Glu Asn Ala Gly Gly Phe Trp Thr Glu
                245                 250                 255

Arg Trp Gly Asp Ala Pro Val His Ser Leu Ala Val Gly Leu Leu Leu
            260                 265                 270

Asn Arg Ser Gln Val His Tyr Phe Arg Asp Leu Gly Tyr Gln His Ser
        275                 280                 285

Thr Ile Gln His Cys Gly Gln Glu Tyr Gly Cys Asn Cys Asp Cys Pro
    290                 295                 300

Phe Asn Ile Pro Asp Tyr Glu Thr Lys Pro Gly Ser Cys Ile Asn Glu
305                 310                 315                 320

Trp Ala Ser Val Met Gly Gly Phe Leu Asp Glu
                325                 330

<210> SEQ ID NO 28
<211> LENGTH: 215
<212> TYPE: PRT
<213> ORGANISM: Schizosaccharomyces pombe

<400> SEQUENCE: 28

Trp Asp Leu Ser Gln Val Lys Pro Leu Val Glu Asn Asn Arg Leu Tyr
1               5                   10                  15

Gln Gln Arg Ala Asp Ala Leu Ala Gln Glu Asn Leu Ser Tyr Val Tyr
            20                  25                  30

Ser Pro Leu Phe His Ser Phe Gln Asp Trp Val Val Arg Ser Leu Leu
        35                  40                  45

Tyr His Pro Gln Leu Glu Tyr Asp Tyr Val Trp Arg Ile Glu Pro Gly
    50                  55                  60
```

```
Leu Lys Leu Val Cys Glu Glu Lys Lys Asp Ile Phe Ser Thr Phe Lys
65                  70              75                  80

Asp Ser Asp Ile Val Phe Thr Asn His Val Cys Glu Arg Lys His Ser
            85              90                  95

Gly Ile Tyr Ala Met Glu Glu Ala Ile Glu Glu Tyr Lys Ile Leu Asn
            100             105             110

Thr Gln Gly Asp Phe Ser Asn Ile Trp Val Tyr Ser Asn Asn Tyr Thr
        115             120             125

Tyr Cys Lys Tyr Trp Pro Phe Asn Glu Ile Leu Ser Leu Lys Gln Ile
    130             135             140

Arg His Asn Gln Thr Tyr Thr Asn Leu Ile Asn Tyr Leu Leu Gly Ser
145                 150             155                 160

Gly Gly Thr Tyr Tyr His Arg Trp Thr Glu Ser Asp Ile Leu Ser Ala
            165             170             175

Ala Phe Gly Val Leu Arg Ala Arg Ala Asn His Met Glu Ser Val Gly
            180             185             190

Phe Phe Leu Asn Asp Asp Val His Tyr Cys Pro Glu Thr Ile Pro Tyr
        195             200             205

Thr Gly Arg Cys Ala Cys Leu
    210             215
```

HOST, TRANSFORMANT AND METHOD FOR PRODUCING THE TRANSFORMANT AND METHOD FOR PRODUCING O-GLYCOSYLATED HETEROLOGOUS PROTEIN

CROSS-REFERENCE TO RELATED APPLICATIONS

The present application is a continuation of International patent application PCT/JP2009/067081, filed on Sep. 30, 2009, which claims priority to Japanese patent applications JP 2009-119280, filed on May 15, 2009 and JP 2003-256354, filed on Oct. 1, 2008.

TECHNICAL FIELD

The present invention relates to a host, a transformant, a method for producing the transformant and a method for producing an O-glycosylated heterologous protein.

BACKGROUND ART

Glycosylation of secretory proteins and the like is one of the important processes in the post-translational modification and controlled by various enzymes in the endoplasmic reticulum and the Goldi apparatus. Sugar chains attached to proteins by glycosylation consist of mannose (Man), galactose (Gal), N-acetylglucosamine and the like. Sugar chains attached to proteins are classified into two groups: N-linked sugar chains linked to the amide nitrogen atom in an asparagine residue and O-linked sugar chains linked to the hydroxyl oxygen atom in a serine or threonine residue. These sugar chains are said to stabilize proteins and have influences on the interaction between proteins and cells. Therefore, development of techniques for production of N-glycosylated proteins has been attempted for production of medicinal products (Patent Documents 1 and 2).

While various findings have been accumulated about N-glycosylation, little is known about O-glycosylation. In living organisms, O-glycosylated proteins are usually produced with sugar chains having various structures, and for production of medicinal products, control of sugar chain structure is important to produce proteins with sugar chains having specific structures. Therefore, techniques for production of proteins having O-linked sugar chains with specific structures with high productivity are demanded.

For production of desired proteins with high productivity, transformants carrying genes encoding heterologous proteins (which are not inherently produced by the host) introduced by genetic engineering are widely used. For production of eukaryotic proteins, eukaryotic microorganisms are considered as the best host, and mostly yeasts are used because they do not contain substances harmful to humans. Among them, the fission yeast *Schizosaccharomyces pombe* (hereinafter referred to as *S. pombe*) is said to be similar to animal cells in cell cycle, the chromosomal structure, RNA splicing and the like, as compared with budding yeasts such as *Schizosaccharomyces cerevisiae* (hereinafter referred to as *S. cerevisiae*) and is considered to produce proteins which have gone through post-translational modifications close to those in animal cells.

O-glycosylation in *S. cerevisiae* is initiated by attachment of mannose to oxygen atoms in serine or threonine residues of proteins catalyzed by O-mannosyltransferase encoded by the PMT gene family (Non-Patent Documents 1 and 2). The subsequent elongation of sugar chains involves α1,2-mannosyltransferase encoded by the KTR gene family and α1,3-mannosyltransferase encoded by the MNN1 gene family (Non-Patent Document 3).

However, the genes involved in elongation of O-linked sugar chains have not been identified.

For production of heterologous proteins in *S. pombe*, promoters, secretion signal genes, multicloning vectors functional in *S. pombe* have been developed. However, because little is known about genes involved in modification of O-linked sugar chains in *S. pombe*, it has been impossible to control the structure of O-linked sugar chains.

Under these circumstances, methods for producing heterologous proteins having specific O-linked sugar chains are demanded.

PRIOR ART DOCUMENTS

Patent Documents

Patent Document 1: JP-A-2004-501642
Patent Document 2: JP-A-2005-514021

Non-Patent Documents

Non-Patent Document 1: Strahl-Bolsinger S, Gentzsch M and Tanner W, Biochim Biophys Acta, 1426, 297-307 (1999).
Non-Patent Document 2: Girrbach V and Strahl S, J Biol Chem, 278, 12554-12562 (2003)
Non-Patent Document 3: Lussier M, Sdicu M and Bussey H, Biochim Biophys Acta, 1426-323-334 (1999)

DISCLOSURE OF INVENTION

Technical Problem

It is an object of the present invention to provide a transformant which can produce a heterologous protein having a structurally controlled O-linked sugar chain having an O-Man-Gal disaccharide structure (in which mannose and galactose are successively attached to an oxygen atom of the heterologous protein) and a method for producing the transformant by using *S. pombe* as the host. It is another object of the present invention to provide an *S. pombe* host for producing the transformant.

It is a still another object of the present invention to provide a method for producing an O-glycosylated heterologous protein by using the transformant.

Solution to Problem

The present invention provides an *S. pombe* host having no omh1 gene or an inactivated omh1 gene for producing a heterologous protein having an O-linked sugar chain having an O-Man-Gal disaccharide structure by expression of the heterologous protein by a genetic engineering technique and subsequent glycosylation of the expressed heterologous protein.

The present invention provides a transformant containing a gene encoding a heterologous protein from an *S. pombe* host having no omh1 gene or an inactivated omh1 gene.

Preferably, the transformant of the present invention further contains a gene encoding a secretion signal functional in the *Schizosaccharomyces pombe* at the 5' end of the gene encoding the heterologous protein.

The wild type of the heterologous protein produced by the transformant of the present invention is preferably an O-glycosylated protein.

The present invention provides a method for producing a transformant comprising introducing a gene encoding a heterologous protein into an *S. pombe* host having no omh1 gene or an inactivated omh1 gene.

In the method for producing a transformant of the present invention, it is preferred that a gene encoding a secretion signal functional in *Schizosaccharomyces pombe* is present at the 5' end of the gene encoding the heterologous protein.

In the method for producing a transformant of the present invention, it is also preferred that the wild type of the heterologous protein is an O-glycosylated protein.

The present invention provides a method for producing an O-gylcosylated heterologous protein comprising culturing the transformant and recovering the produced O-glycosylated heterologous protein having an O-linked sugar chain having an O-Man-Gal disaccharide structure.

In the method for producing an O-gylcosylated heterologous protein of the present invention, it is preferred that the O-linked sugar chain of the produced O-glycosylated heterologous protein has an O-Man-Gal disaccharide structure irrespective of whether or not the wide type of the heterologous protein is glycosylated and the structure of the sugar chain in the wide type of the heterologous protein.

In the method for producing an O-gylcosylated heterologous protein of the present invention, it is preferred that the O-glycosylated heterologous protein is recovered from the culture of the transformant.

Advantageous Effects of Invention

The *S. pombe* host of the present invention is useful as a host for producing an O-glycosylated heterologous protein having an O-linked sugar chain having an O-Man-Gal disaccharide structure.

By using the transformant of the present invention from an *S. pombe* host, it is possible to produce an O-glycosylated protein having a structurally controlled O-linked sugar chain having an O-Man-Gal disaccharide structure.

According to the method of the present invention for producing a transformant, it is possible to obtain a transformant which produces an O-glycosylated heterologous protein having a structurally controlled O-linked sugar chain having an O-Man-Gal disaccharide structure.

According to the present invention, it is possible to produce an O-glycosylated heterologous protein having a structurally controlled O-linked sugar chain having an O-Man-Gal disaccharide structure by using the transformant.

BRIEF DESCRIPTION OF DRAWINGS

FIG. 1 Amino acid sequences of the proteins encoded by the KTR family and omh genes (SEQ ID NOS: 20-28, respectively, in order of appearance).

DESCRIPTION OF EMBODIMENTS

Figure 2:
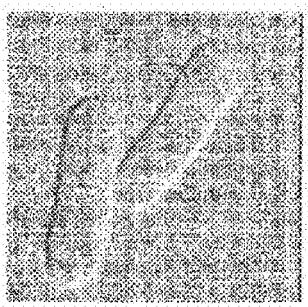
FIG. 2 Cell morphology observed in Example 2.
Figure 2:
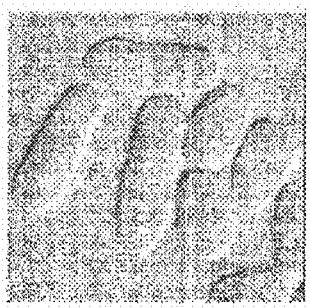
Figure 2:
Figure 2:
Figure 2:
Figure 2:
Figure 2:

The host of the present invention is an *S. pombe* strain having no omh1 gene or an inactivated omh1 gene and is useful for producing the transformant of the present invention. The transformant of the present invention is produced by introducing a gene encoding a heterologous protein (hereinafter referred to also as a "heterologous protein gene"). The transformant of the present invention produces an O-glycosylated heterologous protein having an O-linked sugar chain having an O-Man-Gal disaccharide structure, and in the method of the present invention for producing a protein, the resulting O-glycosylated heterologous protein is recovered.

In the present invention, a "heterologous protein" means a protein extrinsic to *S. pombe* as the host (which no gene in wild type *S. pombe* encodes). The heterologous protein is preferably a protein produced by a human or a mammal in view of industrial value. The "wild type of a heterologous protein" means the protein produced by cells of the organism (other than *S. pombe*) which produces the heterologous protein. The heterologous protein produced by the transformant of the present invention may have a sugar chain different from that of the wild-type heterologous protein. The heterologous protein produced by the transformant of the present invention is an O-glycosylated heterologous protein having an O-linked sugar chain having an O-Man-Gal disaccharide structure and has substantially no O-linked sugar chains that do not have an O-Man-Gal disaccharide structure.

The heterologous protein gene is preferably a gene encoding a protein whose wild type has an O-linked sugar chain because it would be easy to obtain an O-glycosylated heterologous protein (glycoprotein) having a structurally controlled O-linked sugar chain having an O-Man-Gal (in which mannose and galactose are successively attached to an oxygen atom) stably. Such heterologous proteins include chitinase, granulocyte colony-stimulating factor (G-CSF) and the like.

Even if the wild type of the heterologous protein is not an O-glycosylated protein, the transformant of the present invention can produce the heterologous protein with an O-linked sugar chain because depending on the secondary or tertiary structure of the heterologous protein, attachment of a secretion signal at the N-terminal of the expressed heterologous protein enables the expressed heterologous protein to be transported the endoplasmic reticulum and the Goldi apparatus. When the wild type of the heterologous protein does not have a secretion signal at the N-terminal, a chimera sequence containing a DNA sequence encoding an appropriate secretion signal may be used.

(Host)

S. pombe as the host is a yeast of the Shizosaccharomyces genus and is remarkably excellent in acid resistance as compared with other yeasts. This microorganism is similar to animal cells in cell cycle, the chromosomal structure, RNA splicing and the like and is considered to produce proteins which have gone through post-translational modifications close to those in animal cells. The S. pombe host of the present invention is a mutant having chromosomes with no omh1 gene or an inactivated omh1 gene. The S. pombe mutant has the above-mentioned characteristics, and a transformant obtained by introducing a heterologous protein gene into the host also retains the above-mentioned characteristics.

The omh1 gene (SPBC19C7.12c, accession number: O60160) is a gene encoding the enzyme (protein) omh1 p, which catalyzes O-glycosylation in S. pombe and plays an important role in it. Herein, accession numbers mean registry numbers in the protein database Uniprot (URL: http://www.Uniprot.org/).

O-glycosylation is initiated by O-mannosyltransferase expressed by the PMT gene family, as in Schizosaccharomyces cerevisiae. These genes are highly conserved from yeasts to multicellular organisms. In S. pombe, O-mannosyltransferases encoded by the PMT gene family attach mannose to a serine or threonine residue in proteins.

In the elongation of sugar chains after the attachment of the first mannose to a protein, α1,2-mannosyltransferase and α1,3-mannosyltransferase encoded by the KTR gene family and the MNN gene family are involved in S. cerevisiae, as previously mentioned. However, the genes of the enzymes involved in the elongation of O-linked sugar chains in S. pombe have not been identified so far.

The present inventors investigated genes (omh genes and α1,2-mannosyltransferase homologues) in the S. pombe chromosomes highly homologous to the KTR gene family members (encoding α1,2-mannosyltransferase) and identified the six genes encoding enzymes involved in the elongation of O-linked sugar chains in S. pombe, SPBC19C7.12c (omh1 gene), SPBC16H5.09c (omh2 gene, accession number: O42944), SPCC777.07 (omh3 gene, accession number: O74546), SPBC1773.08c (omh4 gene, accession number: O94565), SPBC32H8.08c (omh5 gene, accession number: Q96WW1) and SPAC959.04c (omh6 gene, accession number: Q9P4X2). No genes highly homologous to the MNN1 genes were found in S. pombe.

Figure 1:
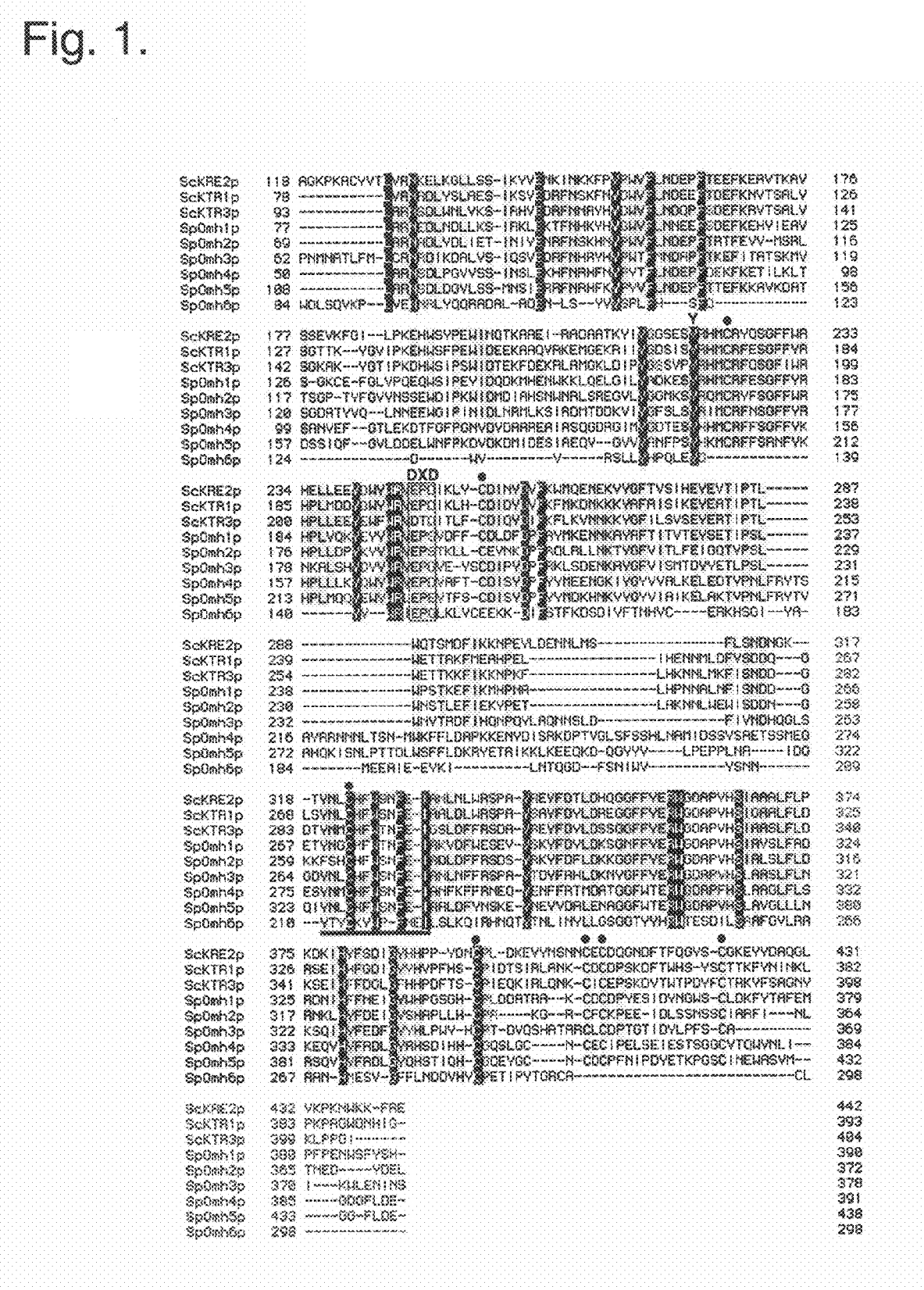

In FIG. 1, the amino acid sequences of the proteins encoded by Kre2 gene, Ktr1 gene and Ktr3 gene in the KTR gene family in S. cerevisiae and by omh1 to omh6 genes are compared.

omh1 to omh6 genes are 33 to 55% homologous to the Kre2 gene, Ktr1 gene and Ktr3 gene subfamilies in the KTR gene family, whereas omh6 gene is less homologous than omh1 to omh6 genes.

The α1,2-mannosyltransferase encoded by Kre2 gene (hereinafter referred to as "Kre2p") has an EPD motif (Glu247-Pro248-Asp249), which corresponds to the DXD motif in various known gylcosyltransferases (FIG. 1). The α1,2-mannosyltransferases encoded by omh1 to omh6 genes (hereinafter referred to as "omh1p" to "omh6p", respectively) have analogous motifs, in which though Asp249 is replaced by Ser, Gly or Glu in some cases, Glu247 is highly conserved, and hence, omh1p to omh6p are involved in the elongation of sugar chains through the same mechanism as Kre2p, which interacts with the phosphate in the donor sugar nucleotide (GDP-mannose) by coordinating with a bivalent cation and plays an important role in sugar exchange with the terminal mannose residue of the acceptor. Like Kre2p, omh1 p to omh6p are considered to be involved in sugar transfer by donating Tyr.

Seven Cys residues (marked with ● in FIG. 1) are also conserved between Kre2p and omh1p to omh6p, and a high degree of conservation between their amino acid sequences is found at many other positions (in the negatively printed positions in FIG. 1), which indicates that omh1p to pmh6p have tertiary structures similar to that of Kre2p.

Furthermore, because the amino acid sequence (YNLCH-FWSNFEI (SEQ ID NO: 1), underlined in FIG. 1) in Kre2p, which acts as the active site for Kre2p to bind to the donor and the acceptor is highly conserved in omh1p to omh6p, too, omh1p to pmh6p are likely to elongate sugar chains in the same manner as Kre2p.

Among these omh genes, omh1 gene encodes an enzyme playing an important role in elongation of O-linked sugar chains. In the transformant of the present invention, because omh1 gene is deleted or inactivated, the transformant cannot express omh1 p, and hence the O-linked sugar chain attached to the heterologous protein produced by the transformant is limited to O-Man-Gal.

This is because omh1p (α1,2-mannosyltransferase) encoded by omh1 gene contributes to attachment of the second mannose to the first mannose attached to the protein. Namely, because deletion or inactivation of omh1 gene makes unable attachment of the second mannose to the first mannose, galactosyltransferase attaches galactose to the first mannose.

None of omh1 gene to omh6 gene are essential for growth of S. pombe, and deletion or inactivation of omh1 gene does not change the phenotype of the cell. Therefore, the transformant of the present invention can stably produce an O-glycosylated heterologous protein despite deletion or inactivation of omh1 gene. In S. pombe, omh2 to omh6 genes do not functionally compensate for the deletion or inactivation of omh1 gene by their overexpression. Since disruption of any one of omh2 to omh5 genes does not inhibit production of the wild-type O-glycosylated protein, these genes seem to encode enzymes which are involved in attachment of the third mannose or have redundant functions in synthesis of sugar chains.

For deletion or inactivation of omh1 gene, conventional methods can be used. Specifically speaking, the Latour system (Nucreic Acids Res (2006) 34: e11 and WO 2007/063919) can be used to delete the gene. Furthermore, the gene can be inactivated by mutating the gene at a certain position by mutant screening using mutagens (Koubo Bunshi Idengaku Jikken-Hou, 1996, Japan Scientific Societies Press), random mutations using PCR (polymerase chain reaction) (PCR Methods Appl., 1992, vol. 2, p. 28-33) and the like.

(Transformant)

The transformant of the present invention is obtained by introducing a heterologous protein gene into the host of the present invention having no omh1 gene or an inactivated ohm1 gene. The heterologous protein gene may have a region encoding a secretion signal in addition to the region encoding the desired heterologous protein. The region encoding a secretion signal encodes a secretion signal functional in cells of the organism which produces the heterologous protein (other than S. pombe), and after the protein is synthesized with the secretion signal at the N-terminal, the secretion signal is shed in the cell, and the heterologous protein is secreted without the secretion signal from the cell. If the heterologous protein inherently has a secretion signal, the secretion signal has to be functional in the host of the present invention. If the secretion signal is not functional in the host of the present invention, it is preferred to use a secretion signal functional in the host instead of the nonfunctional secretion signal.

The secretion signal functional in the host of the present invention is preferably a secretion signal intrinsic to *S. pombe*. The heterologous protein gene having the gene encoding a secretion signal intrinsic to *S. pombe* at the 5-end expresses the heterologous protein having the secretion signal at the N-terminal, and then, the secretion signal is shed off in the host of the present invention. As the secretion signal gene functional in *S. pombe*, the secretion signal genes described in WO 96/23890 are preferred, and especially it is preferred to use the gene encoding the secretion signal P3 described therein.

For transformation of the host, an expression vector carrying the heterologous protein gene is used. When the heterologous protein gene has a secretion signal gene functional in the host, it is preferred to attach a secretion signal gene functional in the host. When the heterologous protein gene contains a secretion signal gene nonfunctional in the host, it is preferred to remove the secretion signal gene and use the heterologous protein gene together with a secretion signal gene functional in the host. The vector has a promoter usually functional in the host and may additionally have at least one of a terminator, a 5'-untranslated region and a 3'-untranslated region. Any promoter functional in *S. pombe* as the host to direct expression of a heterologous protein may be used.

In the present invention, as the promoter, for example, the promoters of animal cell viruses disclosed in JP-A-5-15380, JP-A-7-163373 and JP-A-10-234375 may be mentioned, and CMV promoter and SV40 promoter are preferred. Various promoters known to function in *S. pombe* disclosed in JP-A-11-192094 and WO 2007/26617 may also be used.

For transformation of *S. pombe* using an expression vector carrying the heterologous protein gene, various methods including those mentioned above are known, and such conventional methods may be used. Specifically speaking, in addition to those mentioned above, vectors disclosed in JP-A-2000-262284, JP-A-2003-310269, JP-A-2005-198612 and the like and transformation using them may be used. To obtain a transformant of the host, not only extrachromosomal introduction of the heterologous protein gene in the form of an expression vector but also chromosomal introduction of the heterologous protein gene in the form of an expression cassette may be used. Such an expression cassette has such a promoter and a secretion signal as mentioned above and the like in addition to the heterologous protein gene, and is integrated into a chromosome of the host by homologous recombination. Transformation of *S. pombe* by chromosomal integration of a heterologous protein gene using an expression cassette is preferably carried out in accordance with JP-A-2000-262284. Because a chromosomally integrated expression cassette is unlikely to drop off the cell, the transformant is unlikely to lose its ability to produce an O-glycosylated heterologous protein during culturing. In chromosomal integration into *S. pombe*, it is preferred to integrate two or more expression cassettes in view of high productivity of the O-glycosylated heterologous protein.

Such a vector as described above is introduced into *S. pombe* cells to transform *S. pombe*. For screening for the resulting transformants, the previously mentioned antibiotic resistant genes and auxotrophic markers may be used.

When a vector containing an antibiotic resistant gene is used, transformants can be selected by using a medium containing the antibiotic. As the antibiotic resistant gene, for example, a neomycin resistant gene may be mentioned. As such an anxotrophic marker, for example, orotidine-phosphate decarboxylase (ura4 gene) and isopropylmalate dehydrogenase gene (leu1 gene) may be mentioned.

When an auxotrophic marker is used, for example, an *S. pombe* host which has been made auxotrophic for uracil by deletion or inactivation of ura4 gene is transformed with a vector containing ura4 gene, and transformants carrying the vector are obtained by screening for loss of uracil auxotrophy.

The screening can be carried out, for example, as follows. After several transformants are selected as viable colonies in a medium which allows screening for an auxotrophic marker as mentioned above, the transformants are grown separately in a liquid medium, and transformants with high expression of the heterologous protein are selected by measuring expression of heterologous protein in each culture. The number of expression cassettes integrated into the chromosomes can be identified by analyzing the genomes of the selected transformants by pulse-field gel electrophoresis.

[Method for Producing O-Glycosylated Heterologous Protein]

The method for producing an O-glycosylated heterologous protein of the present invention comprises culturing the transformant of the present invention and recovering the O-gylcosylated heterologous protein produced by the transformant.

As the culture medium, a known culture medium for yeasts may be used as long as it contains carbon sources, nitrogen sources, inorganic salts and the like which *S. pombe* can use and *S. pombe* grows in it efficiently.

The culture medium may be natural or synthetic.

As the carbon sources, saccharides such as glucose, fructose and sucrose, carbohydrates such as starch may, for example, be mentioned. Among them, glucose or sucrose is preferred.

As the nitrogen sources, inorganic ammonium salts such as ammonia, ammonium sulfate, ammonium chloride, ammonium acetate, peptone, meat extract and yeast extract may, for example, be mentioned. Among them, ammonium sulfate or yeast extract is preferred.

As the inorganic salts, magnesium phosphate, magnesium sulfate and sodium chloride are mentioned. Among them, magnesium phosphate is preferred.

The culture medium may contain proteolipid.

Incubation may be carried out with shaking or stirring.

The incubation temperature is preferably 16 to 37° C., particularly 25 to 32° C. The incubation time may be set appropriately.

Incubation may be carried out batch-wise or continuously.

Continuous incubation is carried out, for example, by harvesting the O-glycosylated heterologous protein from the culture after a certain period of incubation, recoverying supernatant and re-incubating the culture after supplementing the supernatant with a culture medium. Continuous incubation improves productivity of the O-glycosylated heterologous protein.

For recovery of the O-glycosylated heterologous protein, known methods for protein isolation may be used.

As described above, according to the present invention, it is possible to produce an O-glycosylated heterologous protein having a structurally controlled O-linked sugar chain having an O-Man-Gal disaccharide structure by using a transformant obtained by using an *S. pombe* host having chromosomes having no ohm1 gene or an inactivated ohm1 gene.

EXAMPLES

Now, the present invention will be described in further detail by reference to specific Examples. However, the present invention is by no means restricted to the following Examples. In the Examples, transformation was carried out by lithium acetate transformation or electroporation.

Example 1

Cloning and Disruption of Omh Genes omh1 to omh6 genes were disrupted by using ura4 as a selectable marker.

Three DNA fragments (1.3 kb, 1.6 kb, 1.25 kb) respectively containing omh1 gene, omh2 gene and omh3 gene, partly or entirely, from the genome of wild-type *S. pombe* were amplified and subcloned into vectors pGEM-T Easy vector and pGEM-T vector (Promega) by using the sense primers and anti-sense primers shown in Table 1.

After subcloning, the vectors were treated with restriction enzymes KpnI and EcoRI to make cuts within omh1 gene, and an ura4⁺ cassette was inserted there to obtain omh1-disrupting vectors. Similarly, omh2-disrupting vectors were prepared by using restriction enzymes EcoRV and HindIII, and omh3-disrupting vectors were prepared by using restriction enzymes EcoRI and XhoI.

*S. pombe* ARC039 strain (haploid), which is incapable of synsthesizing uracil, was transformed with linear DNA fragments from the omh1-disrupting vectors, and an omh1 mutant having a disrupted omh1 gene was obtained by screening in an uracil-selective medium. An omh2 mutants having a disrupted omh2 gene and an omh3 mutant having a disrupted omh3 gene were prepared similarly. It was confirmed by southern blotting and PCR that the desired omh1 mutant, omh2 mutant and omh3 mutant were obtained.

For disruption of omh4 to omh6 genes, an loxP cassette vector (pBS loxP-ura4-loxP, Biosci Biotechnol Biochem, 68, 545-550 (2004)) was used.

An upstream fragment in omh4 gene was amplified by PCR using a sense primer and an anti-sense primer having XhoI and HindIII sites, respectively (Table 1), and a downstream fragment in omh4 gene was amplified by PCR using a sense primer and an anti-sense primer having EcoRI and BamHI sites, respectively. The resulting amplified fragments were trimmed with appropriate restriction enzymes and inserted into pBS loxP-ura4-loxP vector to obtain an omh4-dirsrupting vector having the loxP-ura4-loxP cassette flanked by the omh4 upstream fragment and the omh4 downstream fragment. Similarly, an omh5-disrupting vector and an omh6-disrupting vector were prepared.

*S. pombe* ARC039 strain (haploid), which is incapable of synsthesizing uracil, was transformed with linear DNA fragments from these vectors, and an omh4 mutant, an omh5 mutant and an omh5 mutant were obtained by screening in an uracil-selective medium.

TABLE 1

(SEQ ID NOS: 2-19, respectively, in order of appearance)

| | | | Primer | |
|---|---|---|---|---|
| omh1-disrupting | Sense | | 5'-ggaagccatattcgaagtactatagtg-3' | |
| | Anti-sense | | 5'-tcaatggattcataaggatcacagtcgc-3' | |
| omh2-disrupting | Sense | | 5'-gaagtggatagcgtctacttttaatggtg-3' | |
| | Anti-sense | | 5'-tcccttctagggcaatgaagaagaggagc-3' | |
| omh3-disrupting | Sense | | 5'-ctggcgtatcttacacaatcgaaccatg-3' | |
| | Anti-sense | | 5'-gctgtcgcatgcgactgtacatccgtagggc-3' | |
| omh4-disrupting | Up-stream | Sense | 5'-gtttctcgagatcccagtgattcagccacc-3' | (XhoI site) |
| | | Anti-sense | 5'-gtttaagcttgcactatcagtagtaagacc-3' | (HindIII site) |
| | Down-stream | Sense | 5'-gtttgaattcgccagagttaaaagctaggg-3' | (EcoRI site) |
| | | Anti-sense | 5'-gtttggatcctgtttggccacaccgtcacc-3' | (BamHI site) |
| omh5-disrupting | Up-stream | Sense | 5'-gtttggatccataatgtgttgactcgcagg-3' | (BamHI site) |
| | | Anti-sense | 5'-gtttgaattctcttctattctctaacgacc-3' | (EcoRI site) |
| | Down-stream | Sense | 5'-gtttaagcttaatacgggtactttacgctc-3' | (HindIII site) |
| | | Anti-sense | 5'-gtttctcgagcatcacatcattaacaggcc-3' | (XhoI site) |
| omh6-disrupting | Up-stream | Sense | 5'-gtttggatcctgtgcattatgaacaaccac-3' | (BamHI site) |
| | | Anti-sense | 5'-gtttgaattcagaagcactcaaattggagc-3' | (EcoRI site) |
| | Down-stream | Sense | 5'-gtttaagcttttgatgaatgagctttacag-3' | (HindIII site) |
| | | Anti-sense | 5'-gtttggtacccttttttgactgcttgttcc-3' | (KpnI site) |

Example 2

Cell Morphology

The omh1 to omh6 mutants obtained in Example 1 were incubated overnight in YES medium (5 ml) at 30° C. and 37° C., and their cell morphologies were observed with an observation system equipped with Norarski optics.

As a control, wild-type *S. pombe* was incubated in the same manner as these mutants, and its cell morphology was observed. The results are shown in FIG. 2 (*a*) to (*g*): (a) wild-type *S. pombe*, (b) omh1 mutant, (c) omh2 mutant, (d) omh3 mutant, (e) omh4 mutant, (f) omh5 mutant and (g) omh6 mutant.

As shown in FIG. 2, omh1 to omh6 mutants were all viable, and thus, it turned out that none of omh1 to omh6 genes was essential for viability. omh1 to omh5 mutants in which one of omh1 to omh5 were disrupted, were the same as wild-type *S. pombe* in cellular phenotype. The fact that the phenotype of omh1 mutant was the same as that of wild-type *S. pombe* indicates that omh1p encoded by omh1 gene is not normally involved in glycosylation essential for assembly and function of the cell wall in wild-type *S. pombe*.

In contrast, omh6 mutant showed a phenotype different from that of the wild type.

Example 3

Temperature Dependence and Antibiotic Resistance (Hygromycin)

Figure 3:
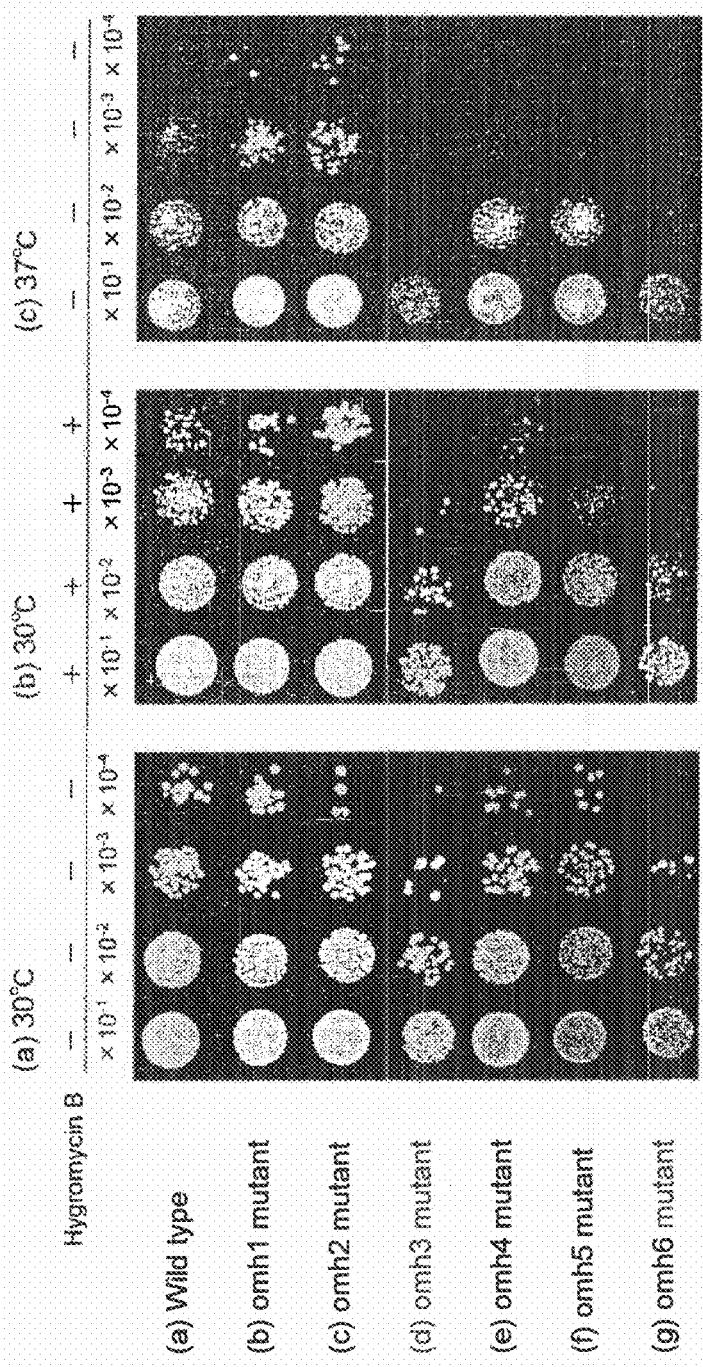
FIG. 3 Cultures obtained in Example 3.

After the incubation in Example 2, each culture was diluted with water to an $OD_{600}$ of 0.5 (cell count $10^7$ cells/ml) and further diluted by a factor of 10 (in the far left column marked with $10^{-1}$ in FIG. 3), and 7 μl of each dilution was spotted onto an YES medium (agar plate) and incubated at 30° C. (FIG. 3(a)) and 37° C. (FIG. 3 (c)) for 3 days. Similarly, each dilution was incubated on YES medium (5 mL) containing 20 μg/l hygromycin B (0.05 mass %) at 30° C. overnight (FIG. 3 (b)). If a rapid growth was observed in a short time, the dilutions were cultured under similar conditions after further serially diluted by a factor of 10. In FIG. 3 (a) to (c), cultures of serial 10-fold dilutions from $OD_{600}$ of 0.5 ($10^{-1}$, $10^{-2}$, $10^{-3}$ and $10^{-4}$) are shown.

As shown in FIG. 3, omh1 mutant, omh2 mutant, omh4 mutant and omh5 mutant were little influenced by temperature or hygromycin B and grew at about the same rate as wild-type S. pombe.

In contrast, the growth of omh3 mutant and omh6 mutant was slower at 37° C. or on a medium containing hygromycin B.

Example 4

Analysis of Acid Phosphatase Assay

The effects of omh1p to omh6p on elongation of N-linked sugar chains were investigated by analysis of acid phosphatases in omh1 mutant to omh6 mutant.

ARC039 strain and omh1 mutant to omh6 mutant were cultured in YES medium (5 ml) at 30° C. to an $OD_{600}$ of 1.5, respectively, and centrifuged to obtain $1.5 \times 10^8$ cells. The cells were resuspended in MMP (the MM disclosed in Methods Enzymol, 194, 795-823 (1991) which contains 14.6 mM sodium acetate instead of disodium hydrogen phosphate and potassium phthalate) and incubated at 30° C. for 3 hours to induce production of an acid phosphatase.

Then, the resulting cells were recovered by centrifugation, washed with Tris-HCI buffer (62.5 mM, pH 6.8) and suspended in 200 μl of an ice-cold lysis solution (62.5 mM Tris-HCVI, pH 6.8, 1 mM EDTA, 2 mM phenylmethylsulfonyl fluoride, 0.1 mM dithiothreitol, 10% (v/v) glycerol) to obtain suspensions.

Figure 4:
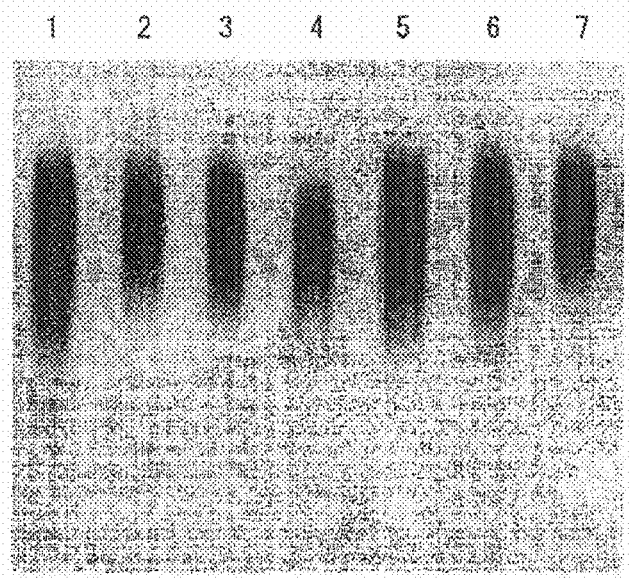
FIG. 4 Analysis of acid phosphatases by nondenaturing PAGE. (Lane 1) wild type *S. pombe*, (Lane 2) omh1 mutant, (Lane 3) omh2 mutant, (Lane 4) omh3 mutant, (Lane 5) omh4 mutant, (Lane 6) omh5 mutant and (Lane 7) omh6 mutant.

The suspensions were stirred with 0.5-mm glass beads by Mini Bead Beater-8 (BioSpec Products) (4° C., 30 sec) 5 times to obtain cell lysates. The cell lysates were electrophoresed on a 6% (w/v) polyacrylamide gel (denatured), and active staining was carried out (Yeast, 18, 903-904 (2001)). The results are shown in FIG. 4. In the results of electorophoresis, Lane 1 wild type S. pombe, Lane 2 omh1 mutant, Lane 3 omh2 mutant, Lane 4 omh3 mutant, Lane 5 omh4 mutant, Lane 6 omh5 mutant and Lane 7 omh6 mutant, respectively.

As shown in FIG. 4, the electrophoretic mobilities of the acid phosphatases produced by omh1 mutant to omh6 mutant were the same as that of the acid phosphatase produced by wild-type S. pombe, which indicates that omh1p to omh6p are not involved with elongation of N-linked sugar chains.

<Structural Analysis of Sugar Chains of Chitinase (Secretory Protein) Heterologously Expressed in Budding Yeast (1)>

Example 5 omh1 mutant was transformed (T. Morita and K. Takegawa, Yeast (2004) 21: 613-617 and JP-A-2005-198612) with a vector pREP41-ScCTS1 containing S. cerevisiae chitinase gene (Cts1) [having a secretion signal gene from S. cerevisiae at the 5' end] and nmt1 promoter from S. pombe (N. Tanaka et al., Biochem Biophys Res commun (2005) 330: 813-820). The transformant was grown in leucine-depleted MM (5 ml) to stationary phase and incubated in 10 ml of a chitinase expression medium (MM containing 0.1% (w/v) glucose and 2% (w/v) fructose instead of 2% (w/v) glucose) at 30° C. for 3 hours. Then, chitinase was recovered from the supernatant of the culture, and the length of the O-linked sugar chain was analyzed by 6% (w/v) polyacrylamide gel SDS (Sodium dodecyl sulfate)-PAGE (Poly-Acrylamide Gel Electrophoresis).

The chitinase was recovered from the culture as follows. The culture was centrifuged after stirred with chitin beads (20 mg, Sigma) at 4° C. for 12 hours, the resulting pellet was washed with a sodium-containing buffer (50 mM Tris-HCI, pH 7.5, 150 mM NaCI) three times, and chitinase was extracted by boiling with a SDS sample buffer (50 μl) for 5 minutes. The gel was stained with Coomassie Brilliant Blue R-250.

Example 6-12

Figure 5:
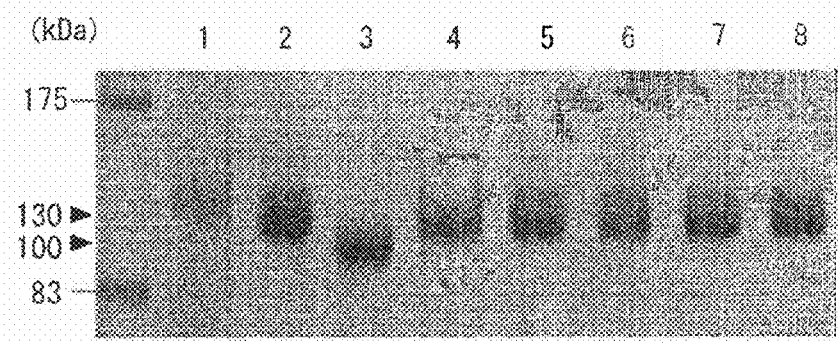
FIG. 5 Analysis of chitinases by SDS-PAGE in Examples 5 to 12. (Lane 1) *S. cerevisiae*, (Lane 2) wild-type *S. pombe*, (Lane 3) omh1 mutant, (Lane 4) omh2 mutant, (Lane 5) omh3 mutant, (Lane 6) omh4 mutant, (Lane 7) omh5 mutant and (Lane 8) omh6 mutant.

Chitinase analysis was carried out for wild-type S. pombe (Example 6), omh2 mutant to omh6 mutant (Examples 7-11) in the same manner as in Example 5. S. cerevisiae (Example 12) was grown in YPD medium (10 ml) at 30° C., and chitinase was extracted and subjected to SDS-PAGE using a 6% (w/v) polyacrylamide gel in the same manner as in Example 5. The results are shown in FIG. 5. In the results of the electrophoresis, Lane 1 S. cerevisiae, Lane 2 wild type S. pombe, Lane 3 omh1 mutant, Lane 4 omh2 mutant, Lane 5 omh3 mutant, Lane 6 omh4 mutant, Lane 7 omh5 mutant and Lane 8 omh6 mutant. The molecular weights of the chitinases were measured by 83-kDa and 175-kDa markers.

As shown in FIG. 5, the chitinases expressed by wild-type S. pombe (Example 6, Lane 2) and S. cerevisiae (Example 12, Lane 1) showed about the same mobilities (corresponding a molecular weight of about 130 kDa). The mobilities of the chitinases expressed by omh2 mutant to omh6 mutant (Example 7 to Example 11, Lanes 4-8) were not influenced and were much the same as that of the chitinase expressed by S. cerevisiae. In contrast, the chitinase expressed by omh1 mutant (Example 5, Lane 3) had a molecular weight of about 100 kDa, and the elongation of O-linked sugar chain had been remarkably inhibited. This confirmed that ohm1 gene is involved in elongation of O-linked sugar chains.

Then, in order to obtain further information about the structure of the O-linked sugar chains, the sugar chains of the glycoproteins (O-glycosylated heteroproteins) produced by wild-type S. pombe and omh1 mutant to omh6 mutant were released by hydrazine treatment, then pyridylaminated (PA) and analyzed by HPLC (High performance liquid chromatography).

Example 13 omh1 mutant was cultured in YES medium at 30° C. to stationary phase, and cell surface galactomannan was extracted from the culture and freeze-dried (Methods Enzymol, 18, 440-470 (1990)). Then, 2 g of the freeze-dried galactomannan was heated with 0.2 ml of anhydrous hydrazine at 60° C. for 6 hours to evaporate hydrazine and passed through a cation exchange resin (Dowex 50W-x2 ($H^+$)) to remove sodium ions. Then, the resulting sample was heated with a pyridylamination agent at 90° C. for 60 minutes and then with a reducing agent (20 µl) at 80° C. for 35 minutes to attach 2-aminopyridine to the reducing terminal of the sugar chain. The excessive pyridylamination agent and reducing agent were removed by phenol/chloroform (volume ratio 50/50) extraction.

The resulting sample was analyzed by normal phase HPLC (column: Asahipak NH2P-50 column (4.6 mm×50 mm), Showa Denko K.K.). The molecular size was determined by using PA (pyridylamino)-labeled markers, PA-mannose, PA-maltose and PA-isomaltooligosaccharide (TAKARA BIO INC.).

Example 14-19

The sugar chains produced by wild-type S. pombe (Example 14) and omh2 mutant to omh6 mutant (Examples 15-19) were analyzed by normal phase HPLC in the same manner as in Example 13. In Example 14, the sugar chains detected as the five main peaks were recovered and treated with jack bean α-mannosidase or coffee bean α-galactosidase to identify the structures of the sugar chains detected as the five peaks by the change in these peaks.

Figure 6:
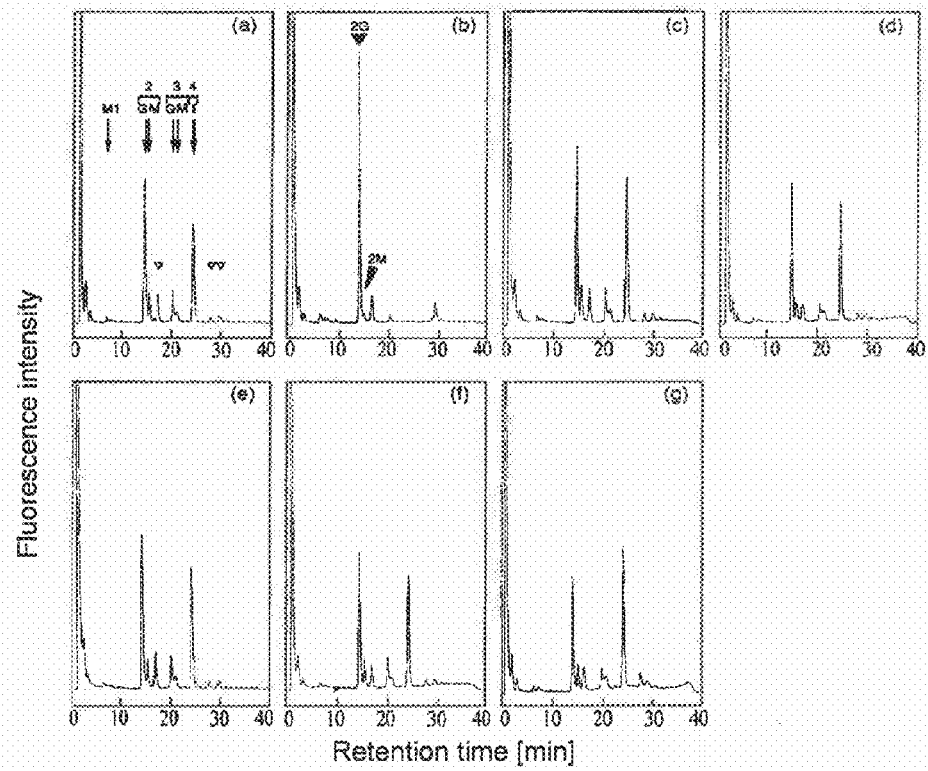
FIG. 6 Sugar chain structure analysis by normal phase HPLC in Examples 13 to 19. (a) wild-type *S. pombe*, (b) omh1 mutant, (c) omh2 mutant, (d) omh3 mutant, (e) omh4 mutant, (f) omh5 mutant and (g) omh6 mutant.

The results of the normal phase HPLC analysis in Examples 13-19 are shown in FIG. 6: (a) wild-type S. pombe, (b) omh1 mutant, (c) omh2 mutant, (d) omh3 mutant, (e) omh4 mutant, (f) omh5 mutant and (g) omh6 mutant.

As shown in FIG. 6, with wild-type S. pombe, five main peaks (2G, 2M, 3G, 3M and 4i) were detected. Peak 2G corresponds to Gal-Man-PA, peak 2M corresponds to Man-Man-PA, peak 3G corresponds to Gal-Man-Man-PA, and peak 3M corresponds to Man-Man-Man-PA. Peak 4i corresponds to a mixture of tetrasaccharide chains.

The sugar chains produced by omh2 mutant to omh6 mutant (FIG. 6 (c) to (g)) were about the same as those produced by wild-type S. pombe (FIG. 6 (a)), and there was no difference between them.

In contrast, omh1 mutant produced much less of tri- or higher saccharide chains, and most of the sugar chains produced by it were detected as peak 2G (FIG. 6 (b)). The sugar chain detected as peak 2G was treated with jack bean α-mannosidase or coffee bean α-galactosidase. It was not degraded by the α-mannosidase, but entirely degraded by the α-galactosidase to Man-PA (corresponding to peak M1 in Fig. (a)).

These results indicate that in omh1 mutant, attachment of the second mannose to the second mannose via an α1,2-bond is inhibited, and that omh1 gene plays an important role in elongation of O-linked sugar chains.

Figure 8:
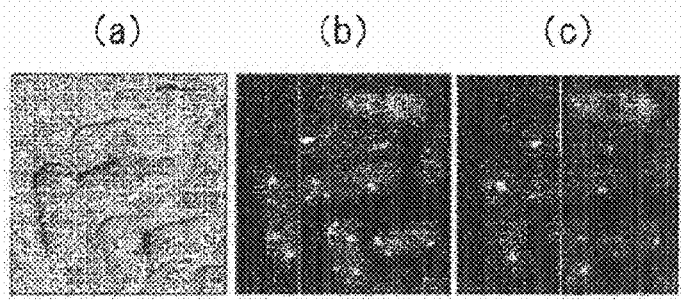
FIG. 8 The results of cell observations in Example 20 with (a) an observation system equipped with Nomarski Interference Contrast, (b) by fluorescence microscopy (with GFP) and (c) by fluorescence microscopy (with RFP).

Example 20 omh1 gene was amplified by PCR from the genome of wild-type S pombe, and restriction sites for BgIII and NotI were introduced. After treatment with these restriction enzymes, the gene was inserted between the these restriction sites in vector pREP41-GFP (vector pTN197 obtained from pREP41, Mol Biol Cell, 12, 3955-3972 (2001)) and cloned to obtain vector pREP41-omh1-GFP having a gene expressing omh1 p having GFP at the C-terminal. Vector pAU-Gms1-RFP having a gene expressing Gms1p (UDP-galactose transporter encoded by Gms1 gene) bonded to RFP (red fluorescent protein) in accordance with Yeast, 18, 745-757 (2001).

omh1 mutant was transformed with pREP41-GFP or pREP41-omh1-GFP, and the transformants were cultured in leucine-depleted MM at 30° C. to stationary phase. Normal phase HPLC analysis was done in the same manner as in Example 13, and the results are shown in FIG. 7(a) (pREP41-GFP) and (b) (pREP41-omh1-GFP).

omh1 mutant was transformed with pREP41-omh1-GFP or pAU-Gms1-RFP, and the transformants were cultured in uracil and leucine-depleted MM at 30° C. The cells were harvested ($OD_{600}$=0.5) and observed. The results are shown in FIG. 8(a) to (c). FIG. 8(a) shows cells observed with an observation system equipped with Nomarski Interference Contrast, FIG. 8(b) shows cells transformed with pREP41-GFP observed by fluorescent microscopy, and FIG. 8(c) shows cells transformed with pAU-Gms1-RFP observed by fluorescent microscopy.

Figure 7:
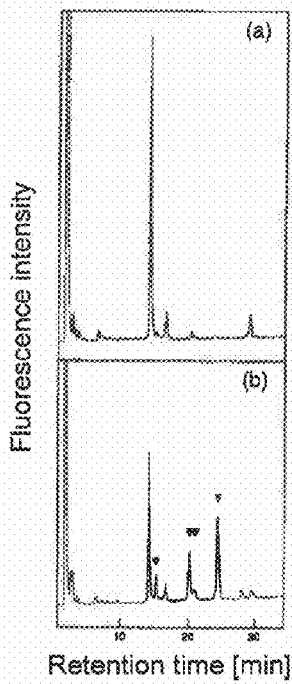
FIG. 7 Sugar chain structure analysis by normal phase HPLC in Example 20. (a) pREP41-GFP and (b) pREP41-omh1-GFP.

As shown in FIG. 7(a), with omh1 mutant carrying pREP41-GFP, the same peaks as in Example 13 were detected, and almost no tri- or higher saccharides were synthesized. In contrast, as shown in FIG. 7(b), with omh1 mutant carrying pREP41-omh1-GFP, the five main peaks as detected with wild-type S. pombe in Example 14 were detected. This is because the expression of omh1 p from the introduced vector enabled attachment of the second mannose to the first mannose.

As shown in FIG. 8(a) to (c), omh1p-GFP (omh1p bound to GFP) colocalized with Gms1p-RFP (Gms1p bound to RFP). Gms1p is a protein which is necessary for glycosylation as a galactose transporter, and from these results, involvement of omh1 gene in O-glycosylation was confirmed.

<Structural Analysis of Sugar Chains of Chitinase Heterologously Expressed in Budding yeast (2)>

Example 21

Wild-type S. pombe was transformed with a vector pFM1-1-ScCts1 containing S. cerevisiae chitinase gene (Cts1), S. pombe invertase promoter and a gene encoding a signal peptide from S. pombe, and the transformant was cultured in 100 ml of leucine-depleted MM (containing 8% (w/v) glucose instead of 2% (w/v) glucose) to stationary phase and then cultured with shaking in 100 ml of a chitinase expression medium (MM containing 0.5% (w/v) glucose and 3% (v/v) glycerol instead of 0.05% (w/v) glucose) with shaking at 30° C. for 12 hours. Then, chitinase was recovered from the supernatant of the culture, and the purity of the chitinase was confirmed by SDS-PAGE using a 6% (w.v) polyacrylamide gel. The chitinase was recovered from the culture as follows. The culture was centrifuged after stirred with chitin (400 mg, Wako Pure Chemical Industries, Ltd.) at 4° C. for 12 hours. The resulting pellet was washed with a sodium-containing buffer (50 mM Tris-HCl, pH 7.5, 150 mM NaCl) three times, and chitinase was extracted by boiling with a SDS sample buffer (50 µl) for 5 minutes.

The gel was stained with Coomassie Brilliant Blue R-250.

Example 22

Chitinase analysis was carried out for omh1 mutant in the same manner as in Example 21.

Figure 9:
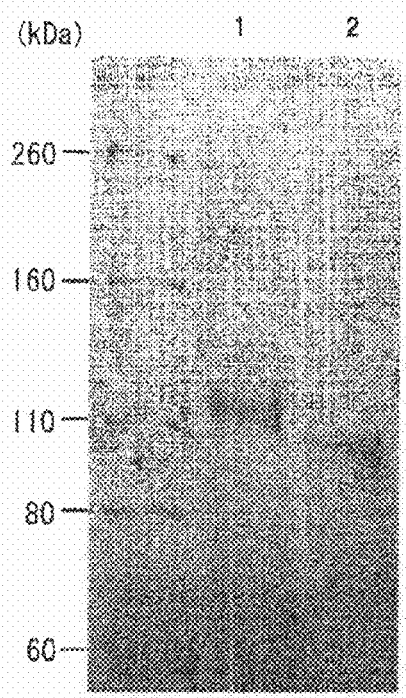
FIG. 9 Analysis of chitinases by SDS-PAGE in Examples 21 and 22. (Lane 1) wild-type *S. pombe* and (Lane 2) omh1 mutant.

The results of Example 21 and Example 22 are shown in FIG. 9: Lane 1 wild-type S. pombe, and Lane 2 omh1 mutant.

As shown in FIG. 9, a single band was detected in Lane 1 and Lane 2, which indicates that the chitinase was isolated from the cultures of wild-type S. pombe and omh1 mutant as a single protein. The chitinase expressed by omh1 mutant had a slightly lower molecular weight, as in Example 6 (FIG. 5, Lane 2).

Then, in order to obtain further information about the structure of the O-linked sugar chains, the sugar chains of the chitinases (O-glycosylated heterologous protein) isolated from the cultures of wild-type *S. pombe* and omh1 mutant were released by hydrazine treatment, then pyridylaminated (PA) and analyzed by HPLC.

Example 23

The chitinase extracted from the chitin in Example 21 was dialyzed against MilliQ water (ultrapure water) to remove SDS and freeze-dried to obtain 1 mg of freeze-dried powder from the culture of wild-type *S. pombe*.

Then, 0.3 mg of the freeze-dried chitinase powder was hydrazinolyzed with Hydraclub C-206 (J-Oil Mills Inc.). The released sugar chain sample was heated with a pyridylamination agent (20 μl) at 90° C. for 60 minutes and then with a reducing agent (20 μl) at 80° C. for 35) to attach 2-aminopyridine to the reducing terminal of the sugar chain. The excessive pyridylamination agent and reducing agent were removed by phenol/chloroform (volume ratio 50/50) extraction.

The resulting sample was analyzed by normal phase HPLC (column: Amide-80 column (4.6 mm×50 mm), Tosoh Corporation). The molecular size was determined by using PA (pyridylamino)-labeled markers, PA-mannose, PA-maltose and PA-isomaltooligosaccharide (TAKARA BIO INC.).

Example 24

The chitinase extracted from the chitin in Example 22 was dialyzed against MilliQ water to remove SDS and freeze-dried to obtain 0.5 mg of freeze-dried powder from the culture of omh1 mutant. Then, normal phase HPLC analysis was carried out in the same manner as in Example 23.

Figure 10:
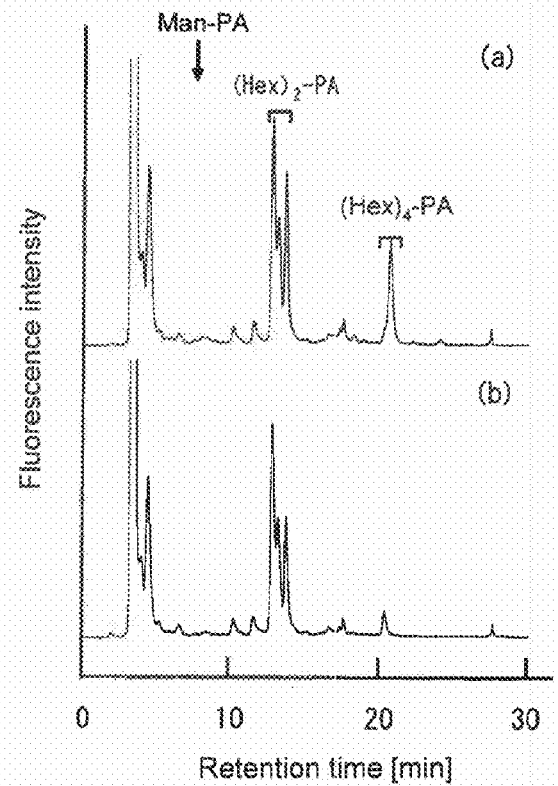
FIG. 10 Sugar chain structure analysis by normal phase HPLC in Examples 23 and 24. (a) wild-type *S. pombe* and (b) omh1 mutant.

The results of normal phase HPLC analysis in Example 23 and Example 24 are shown in FIG. 10: (a) wild-type *S. pombe* and (b) omh1 mutant.

As shown in FIG. 10(*a*), with wild-type *S. pombe*, main peaks corresponding to a disaccharide ((Hex)$_2$-PA in FIG. 10) and a tetrasaccharide ((Hex)$_4$-PA in FIG. 10) were detected. In contrast, as shown in FIG. 10(*b*), with omh1 mutant, only a peak corresponding to the disaccharide was detected.

Example 25

For detailed structural analysis of the disaccharides from wild-type *S. pombe* and omh1 mutant (in Example 23 and Example 24, respectively), the disaccharides corresponding to detected peaks were isolated and analyzed by reverse phase HPLC (column: ODS-80Ts column (4.6 mm×50 mm), Tosoh Corporation). The isolated disaccharides were digested with α-galactosidase (from coffee beans, G8507, Sigma) or α-mannosidase (from jack beans, M7257, Sigma), and the digestion products were analyzed by reverse phase HPLC similarly.

Figure 11:
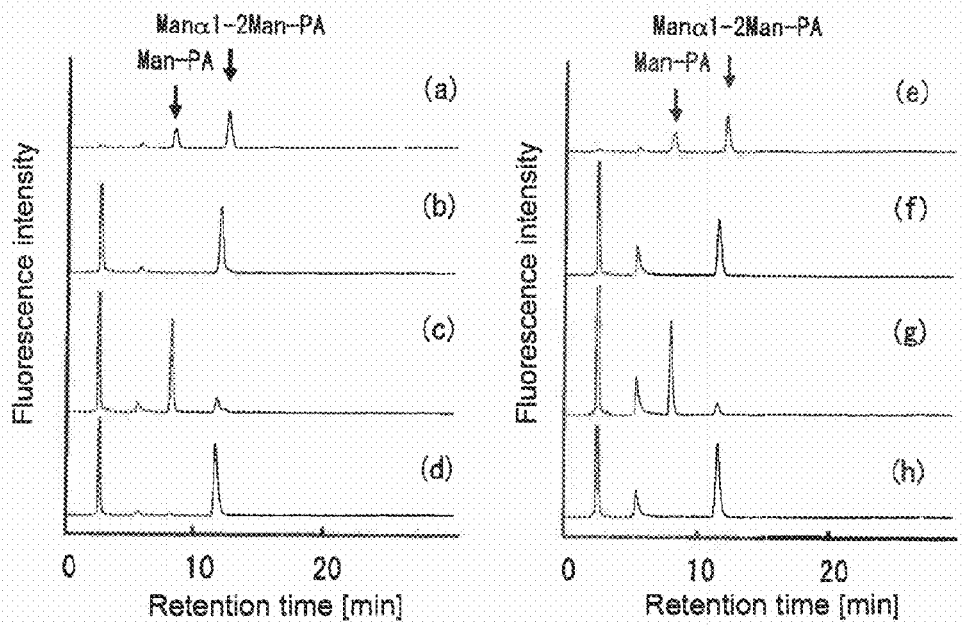
FIG. 11 Sugar chain structure analysis of the disaccharides isolated in Example 25 by reverse phase HPLC. (a) and (e) standard sugar chains, (b) to (d) wild-type *S. pombe* and (f) to (h) omh1 mutant.

The results of reverse phase HPLC analysis are shown in FIG. 11. FIG. 11(*a*) and (*e*) show the retention times of Man-PA and Man-Man-PA (Manα1-2Man-PA) used as standard sugar chains. FIG. 11(*b*) to (*d*) show the results of the analysis of the sugar chains produced by wild-type *S. pombe*, and FIG. 11(*f*) to (*h*) show the results of the analysis of the sugar chains produced by omh1 mutant. FIGS. 11(*b*) and (*f*) show the results of the sugar chain analysis after isolation, FIGS. 11(*c*) and (*g*) show the results of the sugar chain analysis after digestion with α-galactosidase, and FIGS. 11(*d*) and (*f*) show the results of the sugar chain analysis after digestion with α-mannosidase.

As shown in Fig. (b) and (f), the disaccharides produced by wild-type *S. pombe* and omh1 mutant appeared almost as single peaks and had retention times different from that of the Manα1-2Man-PA standard sugar chain. The disaccharide samples from both strains were not degraded by α-mannosidase treatment (FIGS. 11 (*d*) and (*h*)) but were entirely degraded by α-galactosidase to Man-Pa (FIGS. 11 (*c*) and (*g*)).

These results indicate that the disaccharides of the chitinase expressed by wild-type *S. pombe* consists mainly of O-Man-Gal, and that the chitinase expressed by ohm1 mutant had only O-Man-Gal sugar chains, and ohm1 mutant expresses a heterologous protein with sugar chains having the same structure as the cell surface galactomannan.

INDUSTRIAL APPLICABILITY

The transformant of the present invention produces a heterologous protein having a structurally controlled O-linked sugar chain. Therefore, the method for producing n O-glycosylated heterologous protein by using the transformant is suitably used in the medical and other fields.

The entire disclosures of Japanese Patent Application No. 2008-256354 filed on Oct. 1, 2008 and Japanese Patent Application No. 2009-119280 filed on May 15, 2009 including specifications, claims, drawings and summaries are incorporated herein by reference in their entireties.

What is claimed is:

1. A *Schizosaccharomyces pombe* host having no omh1 gene or an inactivated omh1 gene and comprising a heterologous gene, wherein the heterologous gene expresses an O-glycosylated heterologous protein having an O-linked sugar chain and an O-Man-Gal disaccharide structure.

2. The *Schizosaccharomyces pombe* host according to claim 1, wherein the heterologous gene is a recombinant fusion further comprising a gene encoding a secretion signal functional in the *Schizosaccharomyces pombe* linked to the 5' end of the heterologous gene.

3. The *Schizosaccharomyces pombe* host according to claim 1, wherein the heterologous protein, in wild type form, produced by the transformant is an O-glycosylated protein.

4. A method for producing the *Schizosaccharomyces pombe* host according to claim 1, the method comprising introducing the heterologous gene into the *Schizosaccharomyces pombe* host having no omh1 gene or an inactivated omh1 gene.

5. The method according to claim 4, wherein the heterologous gene is a recombinant fusion further comprising a gene encoding a secretion signal functional in *Schizosaccharomyces pombe* linked to-the 5' end of the gene.

6. The method according to claim 4, wherein the heterologous protein, in wild type form, is an O-glycosylated protein.

7. A method for producing an O-glycosylated heterologous protein, the method comprising culturing the *Schizosaccharomyces pombe* host of claim 1 to produce an O-glycosylated heterologous protein having an O-linked sugar chain and an O-Man-Gal disaccharide structure.

8. The method for producing an O-glycosylated heterologous protein according to claim 7, wherein the O-linked sugar chain of the produced O-glycosylated heterologous protein has an O-Man-Gal disaccharide structure irrespective of whether a wild type of the heterologous protein is glycosylated and the structure of the sugar chain in the wide type of the heterologous protein.

9. The method for producing an O-glycosylated heterologous protein according to claim 7, further comprising recovering the O-glycosylated heterologous protein.

10. The *Schizosaccharomyces pombe* host according to claim 1, which has no omh1 gene.

11. The *Schizosaccharomyces pombe* host according to claim 1, which has an inactivated omh1 gene.

* * * * *